US010166353B2

(12) United States Patent
Pecherer

(10) Patent No.: US 10,166,353 B2
(45) Date of Patent: Jan. 1, 2019

(54) TOOL AND METHOD FOR INSERTING AN ENDOTRACHEAL TUBE

(71) Applicant: Evgeny Pecherer, Netanya (IL)

(72) Inventor: Evgeny Pecherer, Netanya (IL)

(*) Notice: Subject to any disclaimer, the term of this patent is extended or adjusted under 35 U.S.C. 154(b) by 937 days.

(21) Appl. No.: 14/434,408

(22) PCT Filed: Oct. 10, 2013

(86) PCT No.: PCT/IB2013/059261
§ 371 (c)(1),
(2) Date: Apr. 9, 2015

(87) PCT Pub. No.: WO2014/057449
PCT Pub. Date: Apr. 17, 2014

(65) Prior Publication Data
US 2015/0258296 A1    Sep. 17, 2015

(30) Foreign Application Priority Data
Oct. 14, 2012  (IL) ......................................... 222433

(51) Int. Cl.
| *A61M 16/04* | (2006.01) |
| *A61B 1/06* | (2006.01) |
| *A61B 1/05* | (2006.01) |
| *A61B 1/00* | (2006.01) |
| *A61B 1/267* | (2006.01) |
| *A61M 25/01* | (2006.01) |

(52) U.S. Cl.
CPC ..... *A61M 16/0488* (2013.01); *A61B 1/00052* (2013.01); *A61B 1/05* (2013.01); *A61B 1/06* (2013.01); *A61B 1/0676* (2013.01); *A61B 1/267* (2013.01); *A61M 16/0434* (2013.01); *A61M 16/04* (2013.01); *A61M 25/0113* (2013.01)

(58) Field of Classification Search
CPC .......... A61M 16/0488; A61M 16/0434; A61M 16/04; A61M 25/0113; A61B 1/00052; A61B 1/05; A61B 1/06; A61B 1/0676; A61B 1/267
See application file for complete search history.

(56) References Cited

U.S. PATENT DOCUMENTS

| 3,985,131 | A |   | 10/1976 | Buck et al. |
| 4,037,588 | A |   | 7/1977 | Heckele |
| 4,574,784 | A | * | 3/1986 | Soloway ................ A61B 1/267 600/193 |

(Continued)

FOREIGN PATENT DOCUMENTS

| GB | 2491189 A | 11/2011 |
| JP | 05329095 A | 12/1993 |

(Continued)

*Primary Examiner* — Gregory Anderson
*Assistant Examiner* — Jonathan Paciorek
(74) *Attorney, Agent, or Firm* — Alphapatent Associates, Ltd; Daniel J. Swirsky

(57) ABSTRACT

A tool for inserting an endotracheal tube, comprising a tubular sheath defining therein a longitudinally extending lumen, is provided. The tool comprises a longitudinal insertion member, and a guide member configured to facilitate relative longitudinal motion between the insertion member and the endotracheal tube when the insertion member is received within its lumen.

19 Claims, 6 Drawing Sheets

(56) References Cited

U.S. PATENT DOCUMENTS

| | | | |
|---|---|---|---|
| 4,722,335 A * | 2/1988 | Vilasi | A61M 16/04 128/207.14 |
| 4,846,153 A * | 7/1989 | Berci | A61B 1/00135 128/200.26 |
| 4,924,862 A | 5/1990 | Levinson | |
| 5,060,633 A | 10/1991 | Gibson | |
| 5,259,377 A | 11/1993 | Schroeder | |
| 5,551,946 A | 9/1996 | Bullard | |
| 5,664,560 A | 9/1997 | Merrick et al. | |
| 5,776,052 A * | 7/1998 | Callahan | A61B 1/267 600/194 |
| 5,800,344 A | 9/1998 | Wood et al. | |
| 6,217,514 B1 | 4/2001 | Gruen et al. | |
| 6,634,356 B1 | 10/2003 | O'Dea et al. | |
| 6,719,688 B2 | 4/2004 | Pecherer et al. | |
| 7,909,759 B2 | 3/2011 | Pecherer | |
| 8,287,450 B1 | 10/2012 | He et al. | |
| 2003/0092967 A1 | 5/2003 | Fourie et al. | |
| 2007/0125374 A1 | 6/2007 | Smith et al. | |
| 2008/0146878 A1 | 6/2008 | Frost | |
| 2008/0242941 A1 | 10/2008 | Kim et al. | |
| 2009/0050146 A1 | 2/2009 | Smith | |
| 2011/0180072 A1 | 7/2011 | Morejon | |
| 2012/0330103 A1 | 12/2012 | Tenger et al. | |
| 2013/0104896 A1 | 5/2013 | Kimm et al. | |

FOREIGN PATENT DOCUMENTS

| | | |
|---|---|---|
| WO | 2010065566 A2 | 6/2010 |
| WO | 2011119521 A1 | 9/2011 |

\* cited by examiner

TOOL AND METHOD FOR INSERTING AN ENDOTRACHEAL TUBE

CROSS-REFERENCE TO RELATED APPLICATIONS

This application is a U.S. National Phase Application under 35 U.S.C. 371 of International Application No. PCT/IB2013/059261, which has an international filing date of Oct. 10, 2013, and which claims priority and benefit from Israel Application Ser. No. 222433, filed Oct. 14, 2012, the contents and disclosure of which are incorporated herein by reference in their entirety.

FIELD OF THE INVENTION

The present disclosure relates to tools and methods for use in intubation procedures. In particular, in relates to tools and methods used to facilitate inserting an endotracheal tube in a patient's trachea.

BACKGROUND OF THE INVENTION

Endotracheal tubes are used in a variety of medical procedures to provide an unobstructed air passage to a patient's trachea. In many emergency situations, it is necessary to intubate a patient as quickly as possible in order to provide a secure airway to the patient's lungs or to permit forced ventilation thereof while preventing introduction of gastric contents. Failure to quickly supply oxygen to the lungs can result in brain damage or death of the patient.

Intubation is often difficult because of an abnormal anatomy encountered in the patient's airway. One of the steps in an intubation procedure is maneuvering the tube into the patient's trachea rather than the patient's esophagus. As endotracheal tubes are generally formed of a soft, pliable material, a stylet or other manipulation device is often used to assist directing the endotracheal tube during intubation.

The user inserts the stylet into the tube and folds one end of the stylet around the outer end of the endotracheal tube. The user then bends the tube and stylet to approximately what the he estimates the contour of the patient's throat is likely to be (usually J-shape). With the help of a laryngoscope, the user inserts the stylet and endotracheal tube into the patient's mouth and throat until it reaches the patient's trachea. It is often difficult for a user to obtain the proper shape with a flexible stylet and to successfully insert the endotracheal tube into the patient's trachea.

If the user fails to intubate the patient on the first attempt, he must remove the tube and stylet from the patient, grasp the tube and stylet, re-bend it accordingly, re-ventilate the patient, and again insert the tube and stylet into the patient.

Mechanical guides have been developed to assist intubation of endotracheal tubes. For example, U.S. Pat. No. 5,259,377 discloses a stylet comprising a flexible member, a collar slidably mounted thereon, a handle mounted at one end of and along the longitudinal axis of the flexible member and a fixed length filament attached to a distal end of the flexible member and the collar. A portion of the stylet is telescopically received within an endotracheal tube. The user may selectively deflect or induce curvature to the endotracheal tube by applying force to the handle along the axis of the flexible member and inducing movement of the handle with respect to the collar when the filament is under tension. Alternatively, the user may selectively deflect the endotracheal tube by inducing movement of the collar with respect to the handle when the filament is under tension.

SUMMARY OF THE INVENTION

According to one aspect of the presently disclosed subject matter, there is provided a tool for inserting a medical tube, for example an endotracheal tube, the medical tube comprising a tubular sheath defining therein a longitudinally extending lumen, the tool comprising:
  a longitudinal insertion member; and
  a guide member configured to facilitate relative longitudinal motion between the insertion member and the medical tube when the insertion member is received within its lumen.

The guide member may comprise a guide wheel having a circumferentially formed engagement arrangement configured to engage with the medical tube, when the insertion member is received within its lumen, to move it longitudinally relative to the insertion member.

According to another aspect of the presently disclosed subject matter, there is provided a tool for inserting a medical tube, for example an endotracheal tube, the medical tube comprising a tubular sheath defining therein a longitudinally extending lumen, the tool comprising:
  a longitudinal insertion member extending between a proximal end and a distal end thereof; and
  a guide member extending between a proximal end, connected to the proximal end of the insertion member, and a distal end thereof, and comprising a guide wheel having a circumferentially formed engagement arrangement configured to engage with the medical tube, when the insertion member is received within its lumen, to move it longitudinally relative to the insertion member.

According to either of the above aspects, the engagement arrangement may be configured to be engaged by a user's finger (such as the thumb) to rotate the guide wheel. It may also/alternatively be configured to be so engaged by any other part of the user's body. Thus, the engagement arrangement is configured to both facilitate rotation of the guide wheel by a user, and moving of the tube by the guide wheel.

At least a portion of the engagement arrangement is knurled. The knurled area of the engagement arrangement may comprise substantially radially extending ridges and/or teeth.

An inner portion of the engagement arrangement may be smaller than an outer portion of the engagement arrangement. For example, the engagement arrangement may comprise two sides sloping from the outer portion toward the inner portion, thereby forming a V-shape.

The knurled area of the engagement arrangement may be formed on a pair of discs.

The insertion member may extend between proximal and distal ends thereof, with the guide member comprising an arm extending between a proximal end, being articulated to the proximal end of the insertion member, and a distal end thereof.

At least the portion of the insertion member adjacent the guide portion may be substantially straight.

The arm of the guide member may be shorter than the insertion member.

The distal end of the arm of the guide member may be adjacent a middle portion of the insertion member.

The insertion portion may be made of a shape-memory material.

The insertion member may comprise an optical tool at a distal end thereof. The optical tool may comprise a video camera, and/or it may comprise a light source.

At least a distal portion of the insertion member may constitute a stylet.

The distal end of the insertion member may be curved.

The tool may further comprise the medical, e.g., endotracheal, tube.

According to a still further aspect of the presently disclosed subject matter, there is provided a method of inserting a medical tube, e.g., an endotracheal tube, in a patient, the method comprising:

- providing a medical tube comprising a tubular sheath defining therein a longitudinally extending lumen;
- providing a tool comprising a longitudinal insertion member, and a guide member configured to facilitate relative longitudinal motion between the insertion member and the medical tube when the insertion member is received within its lumen;
- inserting the medical tube, with the distal end of the insertion member received therein, into the patient, e.g., into the mouth of the patient toward the tracheal opening; and
- utilizing the guide member to move the insertion member longitudinally relative to the medical tube.

The guide member may comprise a guide wheel having a circumferentially formed engagement arrangement configured to engage with the medical tube, when the insertion member is received within its lumen, to move it longitudinally relative to the insertion member.

The engagement arrangement may be configured to be engaged by a user's finger (such as the thumb) to rotate the guide wheel. It may also/alternatively be configured to be so engaged by any other part of the user's body. Thus, the engagement arrangement is configured to both facilitate rotation of the guide wheel by a user, and moving of the tube by the guide wheel.

At least a portion of the engagement arrangement is knurled. The knurled area of the engagement arrangement may comprise substantially radially extending ridges and/or teeth.

An inner portion of the engagement arrangement may be smaller than an outer portion of the engagement arrangement. For example, the engagement arrangement may comprise two sides sloping from the outer portion toward the inner portion, thereby forming a V-shape.

The knurled area of the engagement arrangement may be formed on a pair of discs.

The insertion member may extend between proximal and distal ends thereof, with the guide member comprising an arm extending between a proximal end, being articulated to the proximal end of the insertion member, and a distal end thereof.

At least the portion of the insertion member adjacent the guide portion may be substantially straight.

The arm of the guide member may be shorter than the insertion member.

The distal end of the arm of the guide member may be adjacent a middle portion of the insertion member.

The insertion portion may be made of a shape-memory material.

The insertion member may comprise an optical tool at a distal end thereof. The optical tool may comprise a video camera, and/or it may comprise a light source.

At least a distal portion of the insertion member may constitute a stylet.

The distal end of the insertion member may be curved.

BRIEF DESCRIPTION OF THE DRAWINGS

In order to understand the invention and to see how it may be carried out in practice, embodiments will now be described, by way of non-limiting examples only, with reference to the accompanying drawings, in which.

DETAILED DESCRIPTION OF EMBODIMENTS

Figure 1:
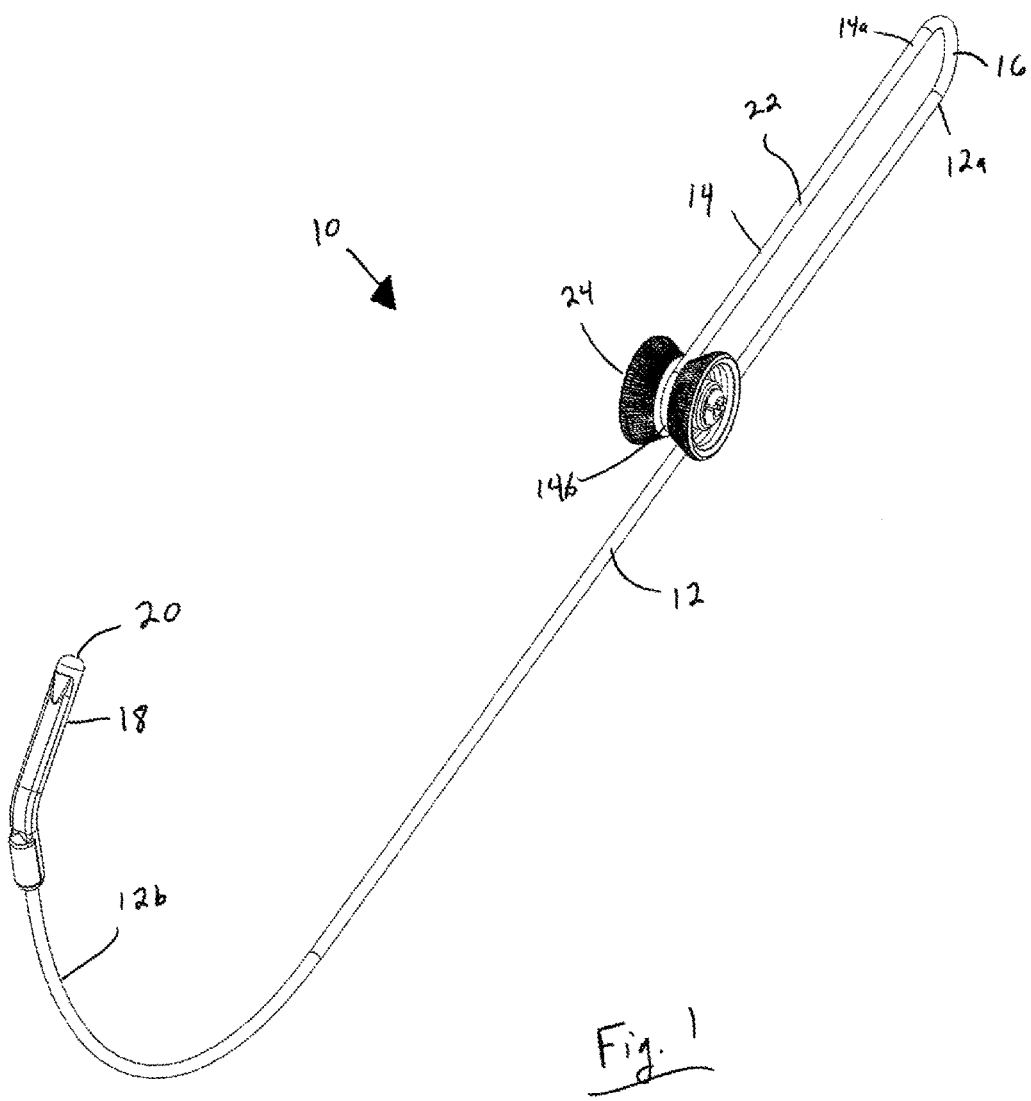
FIG. 1 is a perspective view of a tool according to presently disclosed subject matter.

As illustrated in FIG. 1, there is provided a tool, which is generally indicated at 10, for inserting an endotracheal tube. The tool 10 comprises a longitudinal insertion member 12 and a guide member 14, which may be disposed substantially parallel to one another. The insertion member 12 and guide member 14 are connected to one another at respective proximal ends 12a, 14a thereof by a bridge member 16.

The elements of the tool may be formed as a single piece, as per the example described herein with reference to FIG. 1. Alternatively, as will be described below, they may be formed from separate pieces articulated to one another.

During use of the tool 10, the insertion member 12 is received within the lumen of an endotracheal tube (not illustrated in FIG. 1), and may serve as a stylet for use during its insertion in the patient. As such, a distal end 12b thereof is curved. A portion of the insertion member 12 adjacent the guide member 14 may be substantially straight. This structure gives the insertion member 12 a J-shape.

The insertion member 12 may be provided with a tip 18 provided at its distal end 12b. The tip 18 may be made from a soft, flexible material such as plastic. In addition, its leading end 20 may be rounded, for example to prevent or reduce injuries during intubation.

The insertion member 12 may be made of any material appropriate for its use as a stylet for use in an intubation procedure. For example, it may be made of a shape memory material, which returns to a cold-forged shape upon being heated after deformation, or a suitable polymer. According to some examples, the insertion member 12 may be made from stainless steel SAE 302 or SAE 304.

The guide member 14 is provided to facilitate relative motion between the tool 10 and an endotracheal tube in whose lumen the insertion member 12 is received therein. As such, it comprises an arm 22 attached to the bridge member 16, and a guide wheel 24 rotationally articulated to its distal end 14b.

Figure 2:
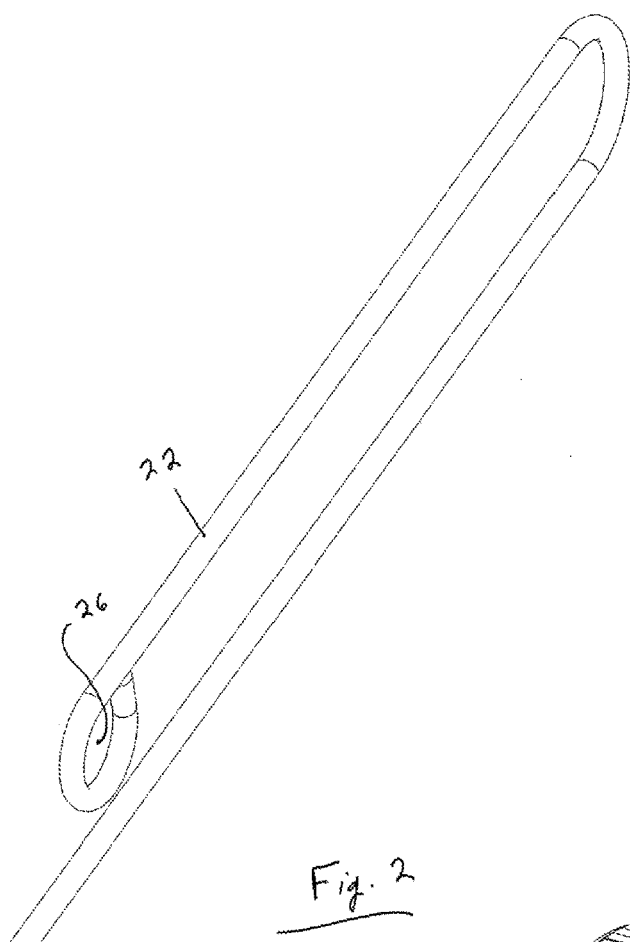
FIG. 2 is a close-up view of a proximal end of the tool illustrated in FIG. 1, with a guide wheel thereof removed.

The arm 22 may be substantially straight and is shorter than the insertion member 12, such that its distal end (which is the distal end 14b of the guide member 14) lies adjacent to a middle portion of the insertion member. As illustrated in FIG. 2, the distal end is formed so as to facilitate retention therein of the guide wheel 24, for example being bent to form an aperture 26. Alternatively, it may be provided with any other suitable arrangement.

Figure 3A:
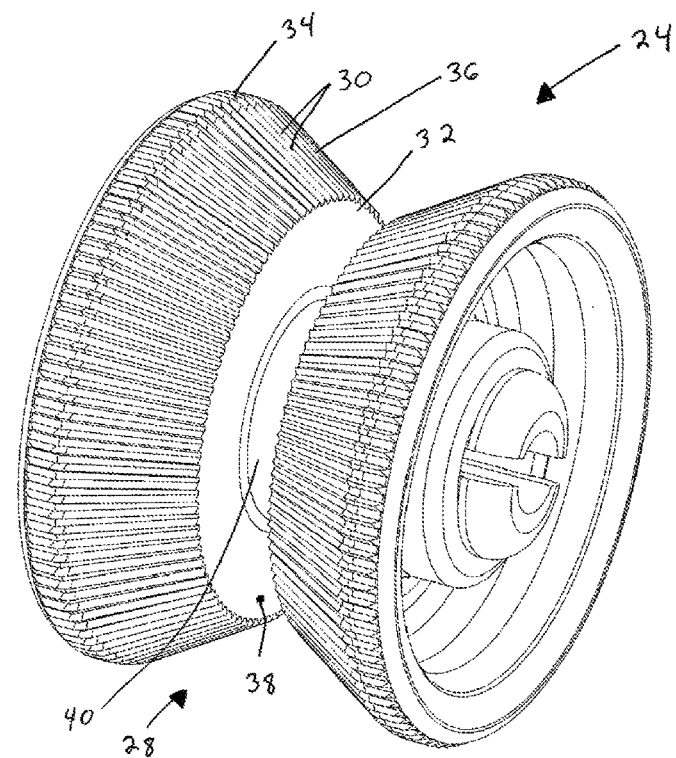
FIGS. 3A and 3B are, respectively, a perspective and an exploded view of a guide wheel of the tool illustrated in FIG. 1.
Figure 3B:
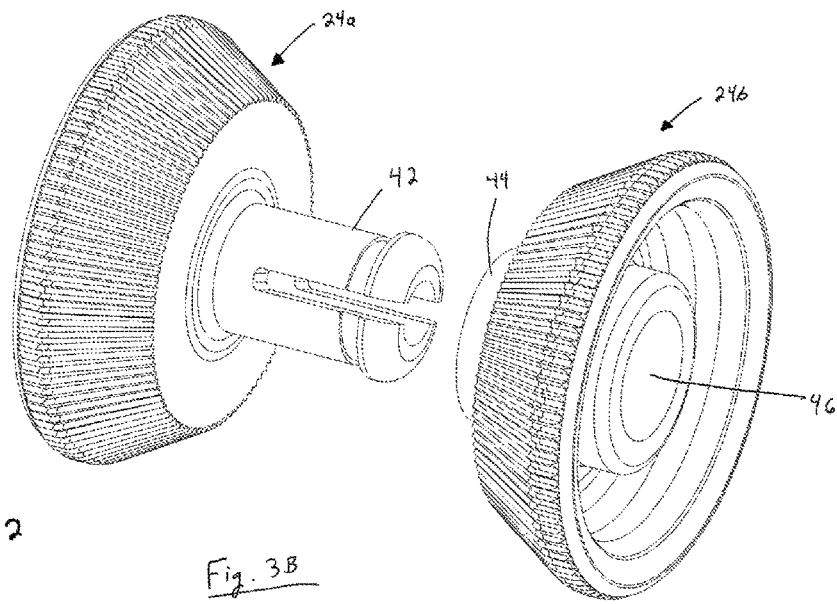

As illustrated in FIGS. 3A and 3B, the guide wheel 24 is configured to engage with the endotracheal tube, when the insertion member 12 is received within its lumen, to move it longitudinally relative to the insertion member. Accordingly, it comprises a circumferentially formed engagement arrangement 28 which is configured to engage with the endotracheal tube to move it longitudinally with the guide wheel 24 is rotated. In addition, engagement arrangement 28 facilitates rotation of the guide wheel 24 by, e.g., a finger of a user.

According to the example illustrated in FIGS. 3A and 3B, the engagement arrangement is knurled. For example, it may comprise a plurality of radially extending ridges 30. In addition, the inner portion 32 of the engagement arrangement 28 may have a smaller radius than outer portions 34 thereof, giving rise to two sides 36 sloping from the outer portion toward the inner portion of the engagement arrangement 28, i.e., it is formed having a V-shape. The sides 36 of the engagement arrangement 28 are spaced from one another, giving rise to a gap 38 which is configured to accommodate the arm 22 of the guide member 14 therein. An axle 40 disposed within the gap 38 is received within the aperture 26.

As best seen in FIG. 3B, the guide wheel 24 is constructed from two pieces 24a, 24b. The first piece 24a comprises half of the engagement arrangement 28, i.e., one of the sides 36 thereof, and a pin 42. The second piece 24b comprises a neck 44 with a through-going aperture 46, sized so as to receive therein the pin 42, formed therein through passing through the second piece. When the two pieces 24a, 24b are assembled, the back 44 constitutes the axle 40 of the guide wheel 24.

Figure 4:
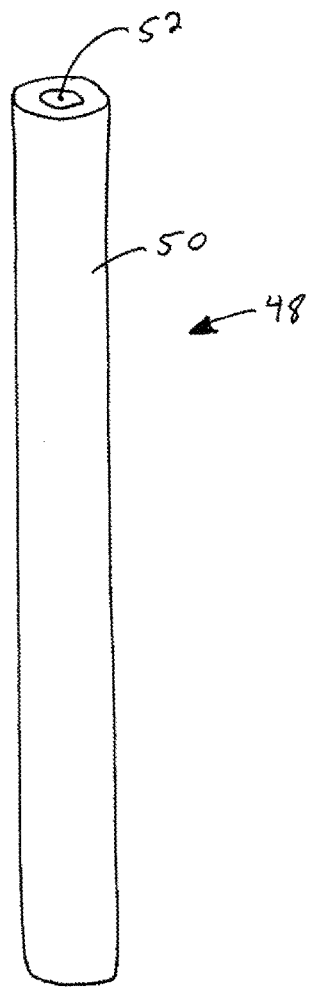
FIG. 4 is a perspective view of an endotracheal tube for use with the tool illustrated in FIG. 1.

The tool 10 as described herein is typically used with endotracheal tube 48, a basic one of which is illustrated in FIG. 4. The endotracheal tube 48 comprises a tubular sheath 50 having a longitudinal lumen 52 passing therethrough. It will be appreciated that, in practice, the endotracheal tube 48 typically comprises additional elements, such as an inflatable cuff near its distal end and an inflating tube near its proximal end. However, for the sake of simplicity, these additional and other elements are not illustrated herein.

Figure 5:
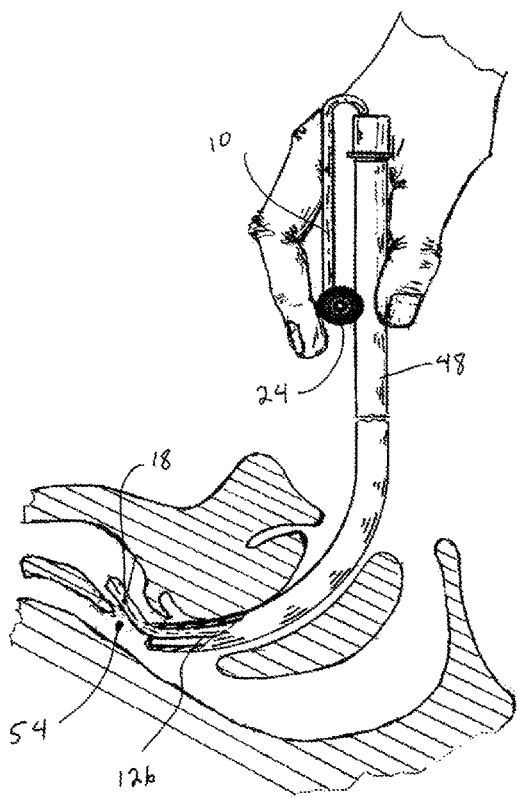
FIG. 5 illustrates a use of the tool illustrated in FIG. 1 with the endotracheal tube illustrated in FIG. 4.

In operation, as illustrated in FIG. 5, a user, who is typically a doctor or other medical professional trained in performing an intubation procedure, inserts the tool 10, with the endotracheal tube 48 mounted thereupon such that insertion member 12 of the tool is received within the lumen 52 of the tube, into a patient's mouth toward the tracheal opening 54, for example with the help of a laryngoscope. The tip 18 may protrude from the distal end of the endotracheal tube 48. The user may then adjust the position of the distal and 12b of the insertion member 12 using the guide wheel 24. In doing so, he presses on the guide wheel 24 and a direction toward the endotracheal tube 48, and rotates it with his finger. The engagement arrangement 28 of the guide wheel 24 bears upon the outside of the endotracheal tube 48, imparting a longitudinal motion thereof along the insertion member 12. Thus, the guide wheel 24 allows the user, during an intubation procedure, to manipulate and adjust the position of a stylet within an endotracheal tube with the same hand that holds the tube.

This longitudinal motion may be used, depending on the configuration of the insertion member 12, to adjust the position of the endotracheal tube 48, to provide a path for the endotracheal tube into the trachea of the patient, or for any other suitable purpose required by the user.

Figure 6:
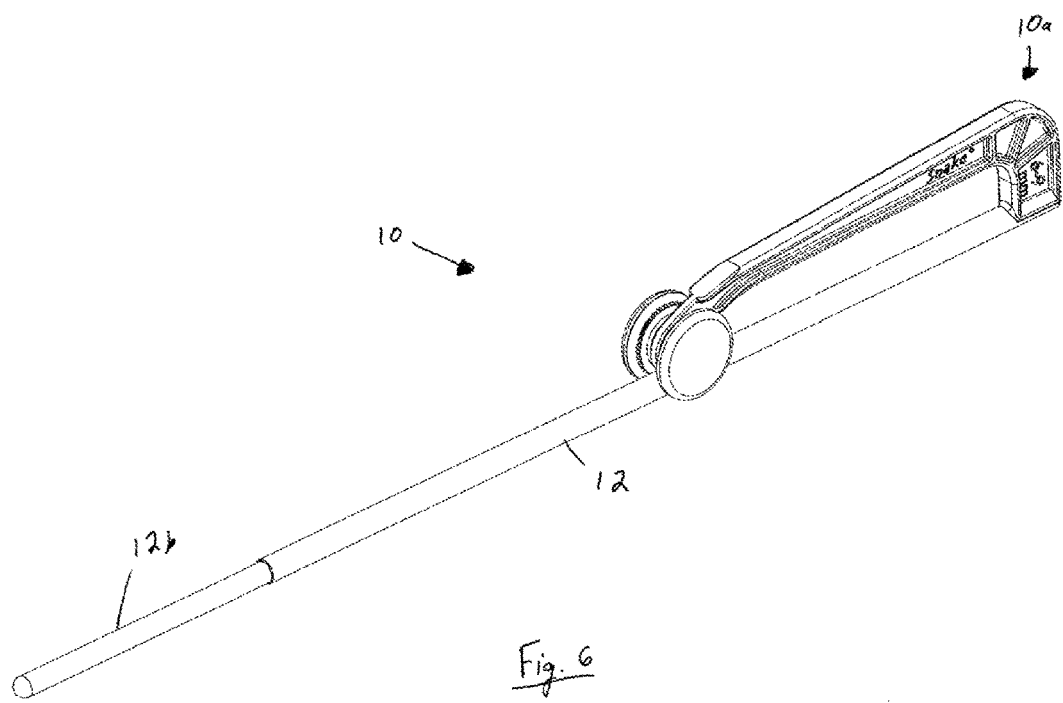
FIG. 6 is a perspective view of another example of a tool according to the presently disclosed subject matter.

Another example of the tool described above with reference to FIGS. 1 through 3B is illustrated in FIG. 6. The proximal end 10a of the tool 10 according to the present example is made from a rigid material such as plastic, for example ABS (acrylonitrile butadiene styrene). The distal end 12b of the insertion member 12 is made from a plastic having a low modulus of elasticity, and may contain a metal core. This allows it to be pre-bent to a shape by a user prior to insertion into a patient.

Figure 7:
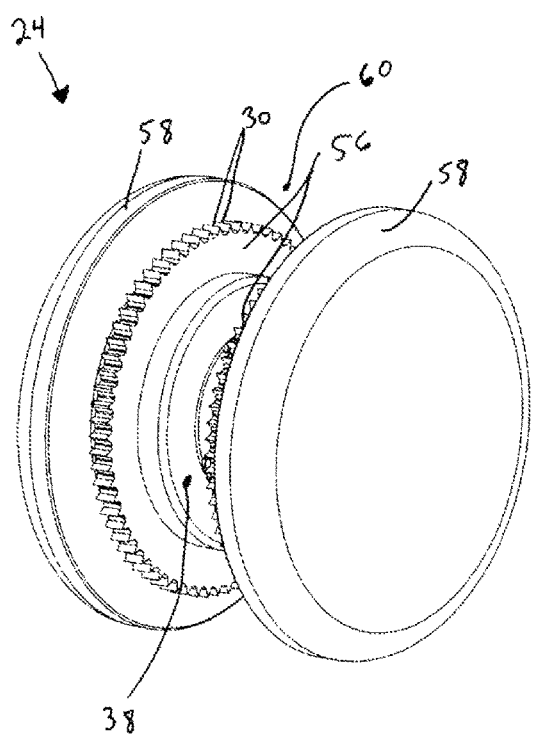
FIG. 7 is a perspective view of a guide wheel of the tool illustrated in FIG. 6.

As illustrated in FIG. 7, the engagement arrangement 28 may comprise a pair of drive discs 56 on either side of a gap 38. The drive discs 56 are circumferentially knurled, for example comprising a plurality of radially formed ridges 30. The engagement arrangement further comprises a pair of positioning discs 58, adjacent the drive discs 56 and exterior thereto. The positioning discs 58 define therebetween a space 60 to accommodate the endotracheal tube during use of the tool 10 (for example as described above), and to maintain its position relative to the drive discs 56.

It will be appreciated that each of that the drive wheels 24 as described above with reference to FIGS. 3A, 3B, and 7 may be used with any of the tools 10 described herein, mutatis mutandis.

The tool may be configured to be integrated with, and/or may include, an optical tool, which may be useful in assisting the user to visualize a patient's anatomy.

Figure 8A:
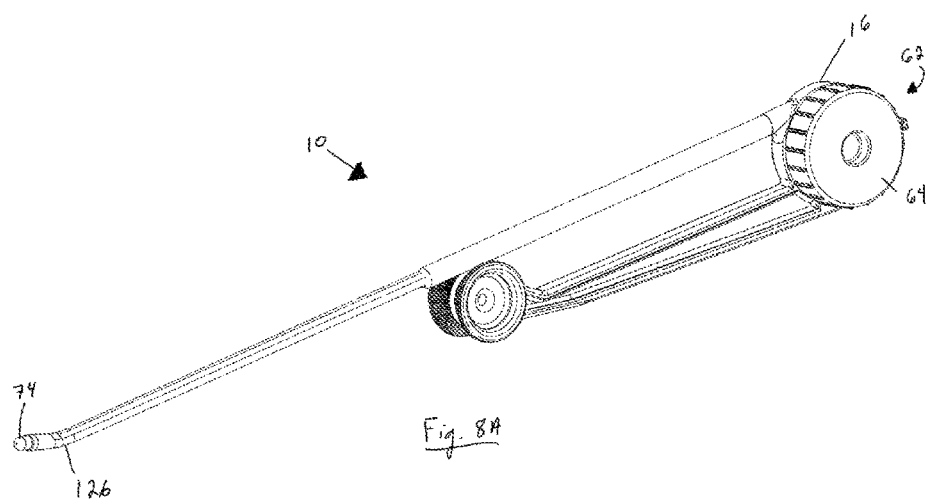
FIG. 8A is a perspective view of a further example of a tool according to the presently disclosed subject matter.
Figure 8B:
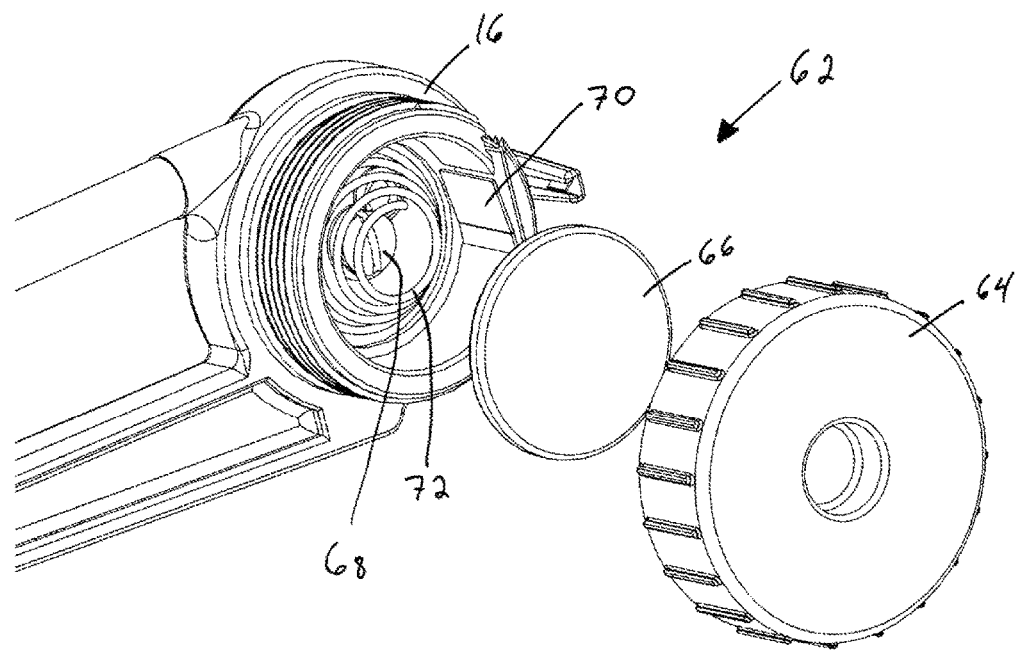
FIG. 8B is a close-up exploded view of a proximal end of the tool illustrated in FIG. 8A.

As illustrated in FIGS. 8A and 8B, the bridge 16 of the tool 10 may comprise a compartment 62 housing elements which constitute part of an optical system. The compartment 62 comprises a cover 64 configured for screwing engagement with the bridge 16, a battery 66, which may be removable such as a coin-battery and which constitutes a power source, a first contact 68 (which may be, for example, the head of a screw), a circumferential second contact 70, and a coil spring 72 configured to bear against the side of the battery, thereby biasing it away from the first contact 68.

The first and second contacts 68, 70 are attached to wires (not illustrated) contained within the insertion member 12, which are connected at their other ends to an optical tool 74 provided at its distal end 12b. The optical tool 74 may be, for example, a light source, such as an LED, and/or a sensor, such as a CMOS or CCD. In the latter case, the distal end 12b of the insertion member 12 may be formed as a lens, constituting, with the sensor, a camera.

The cover 64 may serve as an on/off switch. When the cover is fully screwed on to the bridge 16, it bears against the battery 66, thereby bringing its side into contact with the first contact 68, closing the circuit and providing power to the optical tool 74 via the wires. In order to cut off power to the optical tool 74, the cover is unscrewed slightly, thereby allowing the coil spring 72 to push the battery 66 until it is no longer in contact with the first contact 68.

Figure 8C:
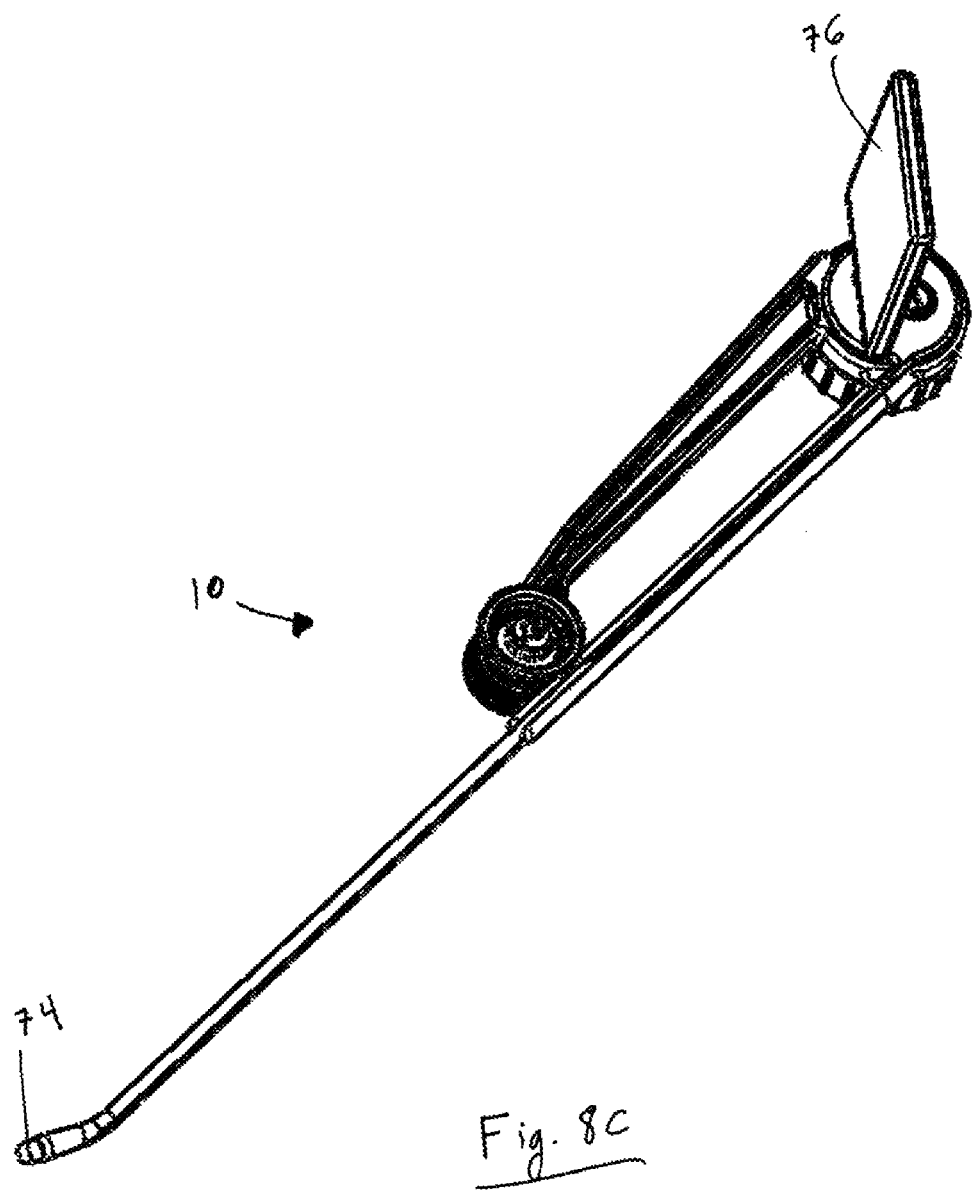
FIG. 8C is a perspective view of a modification of the tool illustrated in FIG. 8A.

In a case wherein the optical tool 74 is a sensor, the tool 10 may be configured to be connected to a viewing system, such as an external monitor. Accordingly, it may be provided with a socket configured to connect to an external viewing system, and/or it may comprise a wireless interface. Alternatively, as illustrated in FIG. 8C, the tool may be provided with a viewing screen 76, which may allow a user look at both the tool and the image returned by the camera. The screen 76 may be tiltable, and may be of any suitable type, such as LCD or OLED.

Those skilled in the art to which this invention pertains will readily appreciate that numerous changes, variations and modifications can be made without departing from the scope of the invention mutatis mutandis. For example, although the present description was directed toward a tool configured for use with an endotracheal tube during an intubation procedure, it may easily be modified for use with other types of medical tubes, such as catheters, etc., for use in other medical procedures, without departing from the spirit and the scope of the presently disclosed subject matter, mutatis mutandis.

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

The scope of the disclosed subject matter is defined by the appended claims and includes both combinations and sub combinations of the various features described hereinabove as well as variations and modifications thereof, which would occur to persons skilled in the art upon reading the foregoing description.

The invention claimed is:

1. A tool for inserting an endotracheal tube, the endotracheal tube comprising a tubular sheath defining therein a longitudinally extending lumen, the tool comprising:
   a longitudinal insertion member; and
   a guide member configured to facilitate relative longitudinal motion between the insertion member and the endotracheal tube when the insertion member is received within its lumen and comprising a guide wheel having a circumferentially formed engagement arrangement configured to engage with the exterior of the endotracheal tube, when the insertion member is received within its lumen, to move it longitudinally relative to said insertion member.

2. The tool according to claim 1, wherein said engagement arrangement is configured to be engaged by a user's finger to rotate the guide wheel.

3. The tool according claim 1, wherein said insertion member is made of a shape-memory material.

4. The tool according to claim 1, wherein said optical tool comprises a light source.

5. The tool according to claim 1, wherein at least a distal portion of said insertion member constitutes a stylet.

6. The tool according to claim 1, wherein the distal end of the insertion member is curved.

7. The tool according to claim 1, further comprising said endotracheal tube.

8. The tool according to claim 1, wherein at least a portion of said engagement arrangement is knurled.

9. The tool according to claim 8, wherein the knurled area of said engagement arrangement comprises substantially radially extending ridges.

10. The tool according to claim 8, wherein the knurled area of said engagement arrangement is formed on a pair of discs.

11. The tool according to claim 1, wherein an inner portion of the engagement arrangement is smaller than an outer portion of the engagement arrangement.

12. The tool according to claim 11, wherein said engagement arrangement comprises two sides sloping from the outer portion toward the inner portion.

13. The tool according to claim 1, said insertion member extending between proximal and distal ends thereof, said guide member comprising an arm extending between a proximal end, being articulated to the proximal end of said insertion member, and a distal end thereof.

14. The tool according to any claim 13, wherein at least the portion of the insertion member adjacent the guide member is substantially straight.

15. The tool according to claim 1, wherein the arm of said guide member is shorter than said insertion member.

16. The tool according to claim 15, wherein the distal end of the arm of said guide member is adjacent a middle portion of said insertion member.

17. The tool according claim 1, wherein said insertion member comprises an optical tool at a distal end thereof.

18. The tool according to claim 17, wherein said optical tool comprises a video camera.

19. A method of inserting an endotracheal tube in a patient, the method comprising:
   providing an endotracheal tube comprising a tubular sheath defining therein a longitudinally extending lumen;

providing a tool comprising a longitudinal insertion member, and a guide member configured to facilitate relative longitudinal motion between the insertion member and the endotracheal tube when the insertion member is received within its lumen and comprising a guide wheel having a circumferentially formed engagement arrangement configured to engage with the exterior of the endotracheal tube, when the insertion member is received within its lumen, to move it longitudinally relative to said insertion member;

inserting said endotracheal tube, with the distal end of the insertion member received therein, into the mouth of said patient toward the tracheal opening; and utilizing the guide member to move the insertion member longitudinally relative to said endotracheal tube.

* * * * *